United States Patent [19]

Bundy

[11] 4,168,386

[45] Sep. 18, 1979

[54] 9-DEOXY-9-METHYLENE-INTER-PHENYLENE-13,14-DIDEHYDRO-16-PHENYL-17,18,19,20-TETRANOR-PGF$_1$ COMPOUNDS

[75] Inventor: Gordon L. Bundy, Portage, Mich.

[73] Assignee: The Upjohn Company, Kalamazoo, Mich.

[21] Appl. No.: 924,033

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ ............................................. C07C 177/00
[52] U.S. Cl. ........................................ 560/61; 560/62; 560/63; 560/55; 260/343; 562/471; 562/472; 562/465

[58] Field of Search ...................... 560/61, 62, 63, 55; 562/465, 471, 472; 260/343

[56] References Cited

PUBLICATIONS

Derwent Abstract 79369y/45.

Primary Examiner—Paul J. Killos
Attorney, Agent, or Firm—Robert A. Armitage

[57] ABSTRACT

The present invention relates to novel 9-deoxy-9-methylene-inter-phenylene-13,14-didehydro-16-phenyl-17,18,19,20-tetranor-PGF$_1$ compounds. These compounds are useful pharmacological agents, and are useful for the same purposes as the corresponding PGE-type compounds.

63 Claims, No Drawings

9-DEOXY-9-METHYLENE-INTER-PHENYLENE-13,14-DIDEHYDRO-16-PHENYL-17,18,19,20-TETRANOR-PGF₁ COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to novel 9-deoxy-9-methylene-inter-phenylene-13,14-didehydro-16-phenyl-17,18,19,20-tetranor-PGF$_1$ compounds, the essential material constituting a disclosure of which is incorporated here by reference from U.S. Pat. No. 4,118,584.

I claim:

1. A prostaglandin analog of the formula

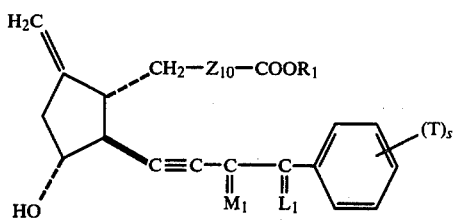

wherein M$_1$ is

or

wherein R$_5$ is hydrogen or methyl;
wherein L$_1$ is

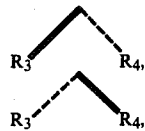

or a mixture of

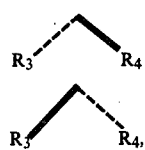

wherein R$_3$ and R$_4$ are hydrogen, methyl, or fluoro, being the same or different, with the proviso that one of R$_3$ and R$_4$ is fluoro only when the other is hydrogen or fluoro;
wherein Z$_{10}$ is

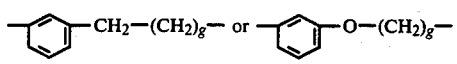

wherein g is one, 2, or 3; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, and the 1,11- or 1,15-lactones thereof.

2. A prostaglandin analog according to claim 1, whererin Z$_{10}$ is

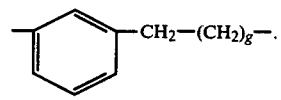

3. A prostaglandin analog according to claim 2, wherein M$_1$ is

4. 9-Deoxy-9-methylene-15-epi-3,7-inter-m-phenylene-16-phenyl-4,5,6,17,18,19,20-heptanor-13,14-didehydro-PGF$_1$, a prostaglandin analog according to claim 3.

5. A prostaglandin analog according to claim 2, wherein M$_1$ is

6. A prostaglandin analog according to claim 5, wherein s is zero or one and T is chloro, fluoro, or trifluoromethyl.

7. A prostaglandin analog according to claim 6, wherein g is 3.

8. 9-Deoxy-9-methylene-2a,2b-dihomo-15-methyl-3,7-inter-m-phenylene-4,5,6,17,18,19,20-heptanor-16-phenyl-13,14-didehydro-PGF$_1$, a prostaglandin analog according to claim 7.

9. 9-Deoxy-9-methylene-2a,2b-dihomo-3,7-inter-m-phenylene-4,5,6,17,18,19,20-heptanor-16-phenyl-13,14-didehydro-PGF$_1$, a prostaglandin analog according to claim 7.

10. A prostaglandin analog according to claim 6, wherein g is one.

11. A prostaglandin analog according to claim 10, wherein at least one of R$_3$ and R$_4$ is methyl.

12. A prostaglandin analog according to claim 11, wherein R$_3$ and R$_4$ are both methyl.

13. 9-Deoxy-9-methylene-16-methyl-3,7-inter-m-phenylene-4,5,6,18,19,20-hexanor-16-phenyl-13,14-didehydro-PGF$_1$, a prostaglandin analog according to claim 12.

14. A prostaglandin analog according to claim 10, wherein at least one of R$_3$ and R$_4$ is fluoro.

15. A prostaglandin analog according to claim 14, wherein R$_3$ and R$_4$ are both fluoro.

16. 9-Deoxy-9-methylene-16,16-difluoro-3,7-inter-m-phenylene-4,5,6,17,18,19,20-heptanor-16-phenyl-13,14-didehydro-PGF$_1$, a prostaglandin analog according to claim 15.

17. A prostaglandin analog according to claim 10, wherein $R_3$ and $R_4$ are both hydrogen.

18. A prostaglandin analog according to claim 17, wherein $R_5$ is methyl.

19. 9-Deoxy-9-methylene-15-methyl-3,7-inter-m-phenylene-4,5,6,17-18,19,20hexanor-16-phenyl-13,14-didehydro-PGF$_1$, a prostaglandin analog according to claim 18.

20. A prostaglandin analog according to claim 17, wherein $R_5$ is hydrogen.

21. 9-Deoxy-9-methylene-3,7-inter-m-phenylene-4,5,6,17,18,19,20-heptanor-16-phenyl-13,14-didehydro-PGF$_1$, a prostaglandin analog according to claim 20.

22. A prostaglandin analog according to claim 1, wherein $Z_{10}$ is

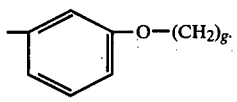

23. A prostaglandin analog according to claim 22, wherein $M_1$ is

24. A prostaglandin analog according to claim 23, wherein s is zero or one and T is chloro, fluoro, or trifluoromethyl.

25. A prostaglandin analog according to claim 24, wherein g is 3.

26. 9-Deoxy-9-methylene-2a,2b-dihomo-15-epi-15-methyl-16-phenyl-3,7-inter-m-phenylene-4,5,6,17,18,19,20-heptanor-13,14-didehydro-3-oxa-PGF$_1$, a prostaglandin analog according to claim 25.

27. 9-Deoxy-9-methylene-2a,2b-dihomo-15-epi-16-phenyl-3,7-inter-m-phenylene-4,5,6,17,18,19,20-heptanor-13,14-didehydro-3-oxa-PGF$_1$, a prostaglandin analog according to claim 25.

28. A prostaglandin analog according to claim 24, wherein g is one.

29. A prostaglandin analog according to claim 28, wherein at least one of $R_3$ and $R_4$ is methyl.

30. 9-Deoxy-9-methylene-15-epi-16-methyl-16-phenyl-3,7-inter-m-phenylene-4,5,6,18,19,20-hexanor-13,14-didehydro-3-oxa-PGF$_1$, a prostaglandin analog according to claim 29.

31. A prostaglandin analog according to claim 28, wherein at least one of $R_3$ and $R_4$ is fluoro.

32. 9-Deoxy-9-methylene-15-epi-16,16-difluoro-16-phenyl-3,7-inter-m-phenylene-4,5,6,17,18,19,20-heptanor-13,14-didehydro-3-oxa-PGF$_1$, a prostaglandin analog according to claim 31.

33. A prostaglandin analog according to claim 28, wherein $R_3$ and $R_4$ are both hydrogen.

34. 9-Deoxy-9-methylene-15-epi-15-methyl-16-phenyl-3,7-inter-m-phenylene-4,5,6,17,18,19,20-heptanor-13,14-didehydro-3-oxa-PGF$_1$, a prostaglandin analog according to claim 33.

35. A prostaglandin analog according to claim 23, wherein $M_1$ is

36. A prostaglandin analog according to claim 35, wherein s is zero or one and T is chloro, fluoro, or trifluoromethyl.

37. A prostaglandin analog according to claim 36, wherein g is 3.

38. A prostaglandin analog according to claim 37, wherein at least one of $R_3$ and $R_4$ is methyl.

39. 9-Deoxy-9-methylene-2a,2b-dihomo-16-methyl-16-phenyl-2,7-inter-m-phenylene-4,5,6,18,19,20-hexanor-13,14-didehydro-3-oxa-PGF$_1$, a prostaglandin analog according to claim 38.

40. A prostaglandin analog according to claim 37, wherein at least one of $R_3$ and $R_4$ is fluoro.

41. 9-Deoxy-9-methylene-2a,2b-dihomo-16,16-difluoro-16-phenyl-3,7-inter-m-phenylene-4,5,6,17,18,19,20-heptanor-13,14-didehydro-3-oxa-PGF$_1$, a prostaglandin analog according to claim 40.

42. A prostaglandin analog according to claim 37, wherein $R_3$ and $R_4$ are both hydrogen.

43. 9-Deoxy-9-methylene-2a,2b-dihomo-16-phenyl-3,7-inter-m-phenylene-4,5,6,17,18,19,20-heptanor-13,14-didehydro-3-oxa-PGF$_1$, a prostaglandin analog according to claim 42.

44. A prostaglandin analog according to claim 36, wherein g is one.

45. A prostaglandin analog accoridng to claim 44, wherein at least one of $R_3$ and $R_4$ is methyl.

46. A prostaglandin analog according to claim 45, wherein $R_3$ and $R_4$ are both methyl.

47. 9-Deoxy-9-methylene-16methyl-16-phenyl-3,7-inter-m-phenylene-4,5,6,18,19,20-hexanor-13,14-didehydro-3oxa-PGF$_1$, tris-(hydroxymethyl)-aminomethane salt, a prostaglandin analog according to claim 46.

48. 9-Deoxy-9-methylene-16-methyl-16-phenyl-3,7-inter-m-phenylene-4,5,6,18,19,20-hexanor-13,14-didehydro-3-oxa-PGF$_1$, methyl ester, a prostaglandin analog according to claim 46.

49. 9-Deoxy-9-methylene-16-methyl-16-phenyl-3,7-inter-m-phenylene-4,5,6,18,19,20-hexanor-13,14-didehydro-3-oxa-PGF$_1$, a prostaglandin analog according to claim 46.

50. A prostaglandin analog according to claim 44, wherein at least one of $R_3$ and $R_4$ is fluoro.

51. A prostaglandin analog according to claim 50, wherein $R_3$ and $R_4$ are both fluoro.

52. A prostaglandin analog according to claim 51, wherein $R_5$ is methyl.

53. 9-Deoxy-9-methylene-15methyl-16,16-difluoro-16-phenyl-3,7-inter-m-phenylene-4,5,6,17,18,19,20-heptanor-13,14-didehydro-3-oxa-PGF$_1$, a prostaglandin analog according to claim 52.

54. A prostaglandin analog according to claim 51, wherein $R_5$ is hydrogen.

55. 9-Deoxy-9-methylene-16,16-difluoro-16-phenyl-3,7-inter-m-phenylene-4,5,6,17,18,19,20-heptanor-13,14-didehydro-3-oxa-PGF$_1$, a prostaglandin analog according to claim 54.

56. A prostaglandin analog according to claim 44, wherein $R_3$ and $R_4$ are both hydrogen.

57. A prostaglandin analog according to claim 56, wherein $R_5$ is methyl.

58. 9-Deoxy-9-methylene-15-methyl-16-phenyl-3,7-inter-m-phenylene-4,5,6,17,18,19,20-heptanor-13,14-didehydro-3-oxa-PGF$_1$, tris-(hydroxymethyl)aminomethane salt, a prostaglandin analog according to claim 57.

59. 9-Deoxy-9-methylene-15-methyl-16phenyl-3,7-inter-m-phenylene-4,5,6,17,18,19,20-heptanor-13,14- didehydro-3oxa-PGF$_1$, methyl ester, a prostaglandin analog according to claim 57.

60. 9-Deoxy-9-methylene-15-methyl-16phenyl-3,7-inter-m-phenylene-4,5,6,17,18,19,20-heptanor-13,14-didehydro-3-oxa-PGF$_1$, a prostaglandin analog according to claim 57.

61. A prostaglandin analog according to claim 56, wherein R$_5$ is hydrogen.

62. 9-Deoxy-9-methylene-16-phenyl-3,7-inter-m-phenylene-4,5,6,17,18,19,20-heptanor-13,14-didehydro-3-oxa-PGF$_1$, methyl ester, a prostaglandin analog according to claim 61.

63. 9-Deoxy-9-methylene-16-phenyl-3,7-inter-m-phenylene-4,5,6,17,18,19,20-heptanor-13,14-didehydro-3-oxa-PGF$_1$, a prostaglandin analog according to claim 61.

* * * * *